United States Patent [19]

Schnur et al.

[11] Patent Number: 4,948,901

[45] Date of Patent: Aug. 14, 1990

[54] BENZAMIDE PROTEASE INHIBITORS

[75] Inventors: Rodney C. Schnur, Mystic; Anton F. J. Fliri, Norwich, both of Conn.

[73] Assignee: Pfizer Inc., New York, N.Y.

[21] Appl. No.: 391,764

[22] Filed: Aug. 9, 1989

Related U.S. Application Data

[62] Division of Ser. No. 197,927, May 24, 1988, Pat. No. 4,874,864.

[51] Int. Cl.$^5$ ............................................. C07D 235/04
[52] U.S. Cl. .................................................... 548/329
[58] Field of Search ........................................ 548/329

[56] References Cited

U.S. PATENT DOCUMENTS 4,563,527  1/1986  Fujii et al. .
4,732,916  3/1988  Satoh et al. .

*Primary Examiner*—John M. Ford
*Assistant Examiner*—J. Richter
*Attorney, Agent, or Firm*—Peter C. Richardson; J. Trevor Lumb; James M. McManus

[57] ABSTRACT

Compounds of the formula

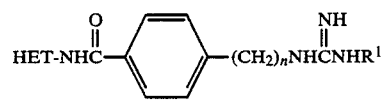

where HET is a heterocyclic group, n is an integer of 0 to 2 and $R^1$ is hydrogen or lower alkyl are protease inhibitors useful as anti-plasmin and antithrombin agents.

7 Claims, No Drawings

BENZAMIDE PROTEASE INHIBITORS

This application is a divisional application of copending application Ser. No. 197,927, filed May 24, 1988, now U.S. Pat. No. 4,874,864.

BACKGROUND OF THE INVENTION

This invention relates to novel benzamide compounds and, in particular, to a series of N-heterocyclic-4-guanylalkylbenzamide useful as protease inhibitors. These compounds have application as protease inhibitors, in particular as antiplasmin agents.

U.S. Pat. No. 4,563,527 claims a series of amidinonaphthyl esters of furoic, benzofuroic and thiophene carboxylic acids as protease inhibitors. U.S. Pat. No. 4,732,916 claims a series of 4-guanylmethylbenzamide derivatives as antiulcer agents.

SUMMARY OF THE INVENTION

It has now been discovered that novel compounds of the formula

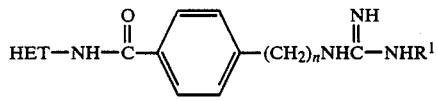

or a pharmaceutically acceptable salt thereof wherein HET is pyrimid-2-yl, dimethylpyrimid-4-yl, thiazol-2-yl, 4-phenylthiazol-2-yl, 4-phenyl-5-carbethoxythiazol-2-yl, 4-biphenylylthiazol-2-yl, pyrazin-2-yl, 6-chloropyrazin-2-yl, quinol-8-yl, 6-methoxyquinol-8-yl, quinol-3-yl, 1,3,4-thiadiazol-2-yl, 3-phenylthiadiazol-2-yl, 5-methylisoxazol-3-yl, 5-chloropyrid-2-yl, 4,5-dicyanoimidazol-2-yl, 5-chlorobenzoxazol-2-yl, indazol-5-yl-2-carbethoxyindol-5-yl or a benzimidazol-2-yl of the formula

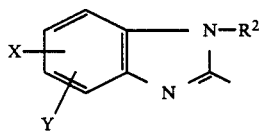

where X is hydrogen or methyl, Y is hydrogen, methyl, benzoyl, nitro, chloro, fluoro, bromo or methoxy and $R^2$ is hydrogen, $(C_1-C_3)$alkyl, phenethyl, phenacyl, N-$(C_1-C_3)$alkylcarbamylmethyl, N,N-di$(C_1-C_3)$alkylcarbamylmethyl, N-$(C_1-C_3)$alkylcarbamyl, $(C_1-C_3)$alkoxycarbonylmethyl or N-(p-chlorobenzyl)carbamylmethyl; n is an integer of 0 to 2; and $R^1$ is hydrogen or $(C_1-C_3)$alkyl are protease inhibitors, having particular application as inhibitors of serine protease and useful as anti-plasmin and anti-thrombin agents.

A preferred group of compounds are those wherein $R^1$ is hydrogen and n is 0. Especially preferred within this group are the compounds where HET is pyrazin-2-yl, pyrimid-2-yl, 1,3,4-thiadiazol-2-yl, quinol-8-yl, thiazol-2-yl or indazol-5-yl.

A second group of preferred compounds are those where HET is a benzimidazol-2-yl of the formula

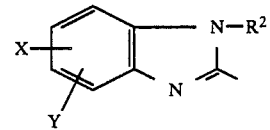

where X is hydrogen. Especially preferred within this group are the compounds where Y and $R^2$ are each hydrogen, where Y is 5-nitro and $R^2$ is hydrogen, where Y is 5-chloro and $R^2$ is hydrogen; or where Y is hydrogen and $R^2$ is N,N-diethylcarbamylmethyl.

As used herein, the term $(C_1-C_3)$alkyl defines alkyl having one to three carbon atoms; similar terms can be used to define alkoxy, etc. Also considered within the scope of the present invention are compounds of the formulae

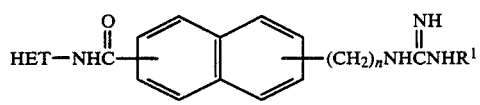

and

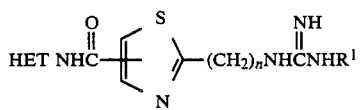

where HET, n and $R^1$ are as herein defined.

DETAILED DESCRIPTION OF THE INVENTION

The compounds of the present invention are prepared by the acylation of the appropriate aminohetercyclic with a carboxy activated benzoic acid derivative.

The activated acid can consist of an acid halide or an activated ester or mixed anhydride. The preferred acylating agent is either the N-hydroxysuccinimide ester or the acid chloride.

The coupling reaction can be achieved by contacting one mole of the appropriate benzoic carboxylic acid N-hydroxysuccinimide ester with from 1 to 2 moles of the requisite aminoheterocyclic and about 0.01 mole of hydroquinone in a reaction-inert solvent such as dimethylformamide, dimethylsulfoxide, or N-methyl-2-pyrrolidone. The reaction is heated in the dark for about 1 to 36 hours at a reaction temperature of 20°–180° C.

On completion of the reaction, the reaction mixture is diluted with methanol, filtered, if necessary, and the filtrate applied to the protonated form of an ionexchange resin (pH 5–6) such as GC 50 (Aldrich Chemical Co., Inc.). The resin-product complex is then loaded on a column and washed sufficiently with methanol, water, dimethylsulfoxide, dimethylformamide or acetonitrile or mixtures thereof, to remove all the remaining, unreacted aminoheterocyclic.

The product is freed from the resin complex by eluting the column with a 0.1–0.01 molar solution of an acid such as hydrochloric acid, hydrobromic acid, methane sulfonic acid, lactic acid or acetic acid in such solvents as water, methanol or acetonitrile. The wash liquids are combined and concentrated. The product, isolated as the salt of the acid wash, precipitates as the solution is concentrated, and is collected by filtration. Further purification can be carried out by recrystallization from such solvents as dimethylformamide, tetrahydrofuran, ethyl acetate, chloroform, dimethylsulfoxide, N-methyl-2-pyrrolidone, diethyl ether or methanol or mixtures thereof.

A modification of this procedure comprises contacting one mole of the 4-guanidinobenzoic acid derivative as an acid addition salt with the silating agent bis-trimethylsilylacetamide, followed by formation of the acid chloride using thionyl chloride. The acid chloride is then treated in tetrahydrofuran with as much as a two-fold excess of the appropriate aminohetercyclic, or a one fold excess plus an excess of an acid scavenger, such as triethylamine.

After a reaction time of about 30 minutes, at ambient temperatures, the reaction is diluted with sufficient water to precipitate the product, which is recrystallized as previously described.

Compounds of the present invention wherein HET is

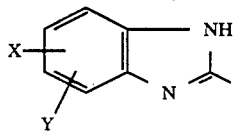

are converted to compounds where HET is

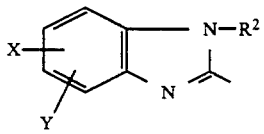

where $R^2$ is as defined, but other than hydrogen.

Acylation of the benzimidazole nitrogen with isocyanates is carried out in a reaction-inert solvent such as dimethylformamide, dimethylsulfoxide, N-methyl-2-pyrrolidone. The reaction can be conducted at from about room temperature to 100° C. Reaction time is about 24 hours and ambient temperatures and 30 minutes to a few hours at elevated temperatures.

When reacting the isocyanate with the compounds identified, it is necessary to use the acid addition salt of the guanidinobenzamide reactant to prevent interaction of the guanyl portion with the isocyanate. Further, it is preferred to use an excess of isocyanate to aid in the completion of the reaction, a ratio of one mole of benzimidazole derivative per five moles of isocyanate provides the desired product.

The reaction mixture, at the end of the reaction period, is diluted with diethyl ether and the precipitated product filtered and purified.

Alkylation of the benzimidazole nitrogen is carried out between one mole of compound containing the benzimidazole moiety and about 5-6 moles of alkylating agent. In addition, the alkylation makes use of from 1 to 4 equivalents of base per mole of starting reagent. Such bases include alkali metal alkoxides and carbonates. The solvent, reaction times and temperature are about the same for the alkylation reaction as for the corresponding acylation reaction.

As previously indicated, the present invention embraces pharmaceutically acceptable salts of the biologically active compounds. Such salts are those which are non-toxic at the dosages administered. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts. Conventional methods of forming acid addition salts may be employed.

Plasmin, a serine protease enzyme existing in the blood, is the result of the action of plasminogen activator on the proenzyme plasminogen. Plasmin plays an important role in capillary blood flow and in the dissolution of fibrin. However, when this enzyme is present in abnormal amounts it causes hemorrhagic diseases. In such cases, the use of an anti-plasmin agent is extremely important. The compounds of the present possess this anti-plasmin activity, which can be readily demonstrated by the assay of H. Zimmerman, et al., *Proc. Natl. Acad. Sci.*, 75, 750 (1978).

The compounds of the present invention can be administered as anti-plasmin agents by either the oral or parental routes of administration, with the former being preferred for reasons of patient convenience and comfort. In general, these anti-plasmin compounds are normally administered orally in dosages ranging from about 6 mg to about 400 mg per kg of body weight per day and 1 mg to about 200 mg per kg of body weight per day when given parenterally; variations will necessarily occur depending upon the condition of the subject being treated and the particular compound being administered. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato and tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be contrued as limiting the same.

EXAMPLE 1

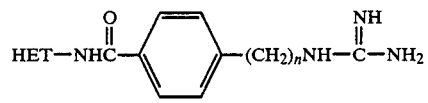

| HET | n | REACTION TIME | REACTION TEMP. °C. | HYDROQUINONE | m.p. °C. |
|---|---|---|---|---|---|
| benzimidazol-2-yl | 0 | 7 hrs | 170 | + | 265–266 |
| 5-NO$_2$-benzimidazol-2-yl | 0 | 7 hrs | 170 | + | 235–237 |
| pyrimidin-2-yl | 0 | 72 hrs | 110 | — | 178–180[a] |
| 6-Cl-pyrazin-2-yl | 0 | 72 hrs | 110 | — | 273 dec. |
| 2,6-(CH$_3$)$_2$-pyrimidin-4-yl | 0 | 120 hrs | 110[b] | — | 238 dec.[a] |
| 4-phenyl-thiazol-2-yl | 0 | 5 hrs | 110 | — | 250–252 |
| 1,3,4-thiadazol-2-yl | 0 | 5 min | 170 | — | 318–320 |
| 3-phenyl-1,2,4-thiadazol-5-yl | 0 | 3 hrs | 170 | — | 308–310[a] |

[a]Purified by column chromatography using chloroform-methanol-acetic acid (18:5:1;V:V:V)
[b]Solvent dimethylformamide 4-Guanidino-N-(pyrazin-2-yl)benzamide hydrochloride
n=0; R$^1$=H; and HET=2-pyrazinul)

A solution of 1.84 g. (19.2 m. mol) of 2-aminopyrzine, 3.0 g. (9.6 m. mol) of 4-quanidinobenzoic acid N-hydroxysiccinimide ester and 300 mg. of hydroquinone in 25 ml. of N-methyl-2-pyrrolidone was heated in the dark under an inert atmosphere at 170° C. for 7 hours. The cooled reaction mixture was diluted with 300 ml. of methanol and 3 ml. of pyridine and treated with 50 g. of CG50 ion exchange resin (H+form). The solution was decanted and treated with an additional 25 g. of resin. The solution was again decanted and treated with 25 g. of resin. The resin fractions were loaded on a column such that the last resin fraction was loaded first, the first, last. The column was eluted with 2 l. of methanol and then with 0.02 N hydrochloric acid in methanol. The fractions containing the product was combined and concentrated in vacuo to a solid. The residue was dissolved in methanol and precipitated with diethyl ether. The product was filtered, washed with i-propanol and dried, 232 mg., m.p. 278°–280° C.

EXAMPLE 2

Using the procedure of Example 1, except where noted, and starting with the appropriate reagents, the following compounds were prepared as the hydrochloride salt:

EXAMPLE 4

4-Guanidino-N-(quinol-8-yl)benzamide
(HET=8-quinolyl; n=0; and R$^1$=H)

A mixture of 200 mg. ( 0.92 m. mol) 4-guanidinobenzoic acid hydrochloride and 190 mg. (0.93 m. mol) of bis-trimethylsilylacetamide in 20 ml. of dry tetrahydrofuran was heated at reflux until a solution was achieved, and then cooled to room temperature. Thionyl chloride (380 mg., 1.86 m. mol) was added and the reaction mixture allowed to stir for 5 min. 8-Aminoquinoline (670 mg., 4.64 m. mol) was added in 5 ml. of tetrahydrofuran and the mixture allowed to stir for 30 min. Water (0.2 ml) was added to the reaction mixture and the solids filtered and dissolved in 60 ml. of methanol and 120 ml. of chloroform. Addition of diethyl ether precipitated the desired product, 153 mg., m.p. 271°–273° C.

EXAMPLE 5

Employing the procedure of Example 4, except where noted, and starting with the requisite reagents, the following products were prepared:

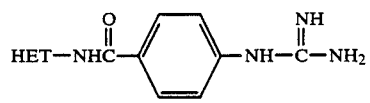

| HET | EQUIV. AMINE/ACID | REACTION TIME | REACTION TEMP. °C. | m.p., °C. |
|---|---|---|---|---|
| 5-methylisoxazol-3-yl | 6:1 | 30 min | 25 | 242–244 |
| 5-chloropyridin-2-yl | 6:1 | 16 hrs | 25 | 255–260 |
| 5-trifluromethyl-1,3,4-thiadiazol-2-yl | 7:1 | 21 hrs | 25 | 326–328 |
| 4-phenyl-5-carbethoxythiazol-2-yl | 7:1 | 24 hrs | 25 | 180–185 |
| 5-(p-nitrophenylsulfonyl)thiazol-2-yl | 5:1 | 2 hrs | 100 | 285 dec.[a] |
| thiazol-2-yl | 5:1 | 30 min | 25 | 175 dec. |
| 4,5-dicyanoimidazol-2-yl | 5:1 | 24 hrs[b] | 25 | 211–215 |
| 5-chlorobenzoxazol-2-yl | 5:1 | 30 min | 25 | 205–210 |
| 4-biphenylylthiazol-2-yl | 5:1 | 48 hrs[c] | 25 | 286–288 |
| indazol-5-yl | 5:1 | 48 hrs[c] | 25 | 285 dec. |
| quinolin-3-yl | 6:1 | 30 min | 25 | 282–285 |
| 5-benzoylbenzimidazol-2-yl | 5:1 | 24 hrs[d] | 25 | 235–240 |
| 5,6-dimethylbenzimidazol-2-yl | 5:1 | 24 hrs[d] | 25 | 233–237 |
| 2-carbethoxyindol-5-yl | 6:1 | 10 min | 25 | 210 dec.[a] |

[a]Purified by column chromatography using chloroform-methanol-acetic acid (18:5:1;V:V:V).
[b]Solvent N-methyl-2-pyrrolidone-tetrahydrofuran (1:5;V:V).
[c]Solvent N-methyl-2-pyrrolidone-tetrahydrofuran (1:2;V:V).
[d]Solvent N-methyl-2-pyrrolidone-tetrahydrofuran (1:4;V:V).

EXAMPLE 6

4-Guanidino-N-(5-chloroimidazol-2-yl)-benzamide
(HET=5-chloroimidazol-2-yl; n=0; and R$^1$=H)

A mixture of 970 mg. (4.48 m. mol) of 4-guanidinobenzoic acid and 910 mg. (4.48 m. mol) of bis-trimethylsilylacetamide in dry tetrahydrofuran was heated to reflux for five minutes. After cooling the resulting solution of thionylchloride, 1.07 g. (8.95 m. mol) was added, followed after 20 minutes by the addition of 1.5 g. (8.95 m. mol) of 2-amino-5-chloroimidazole and 1.81 g. (17.9 m. mol) of triethyl amine in 10 ml. of tetrahydrofuran. After 16 hours at room temperature 0.40 ml. of water was added and the solids filtered, washed with chloroform and recrystallized from methanol-chloroform-diethyl ether, 435 mg., m.p. 263°–265° C.

EXAMPLE 7

Employing the procedure of Example 6, and starting with the appropriate reagents, the following compounds were prepared:

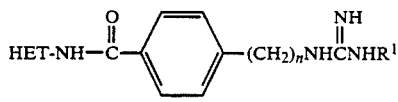

| HET | EQUIV AMINE/ACID | EQUIV TEA$^a$/ACID | REACTION TIME | REACTION TEMP. °C. | m.p., °C. |
|---|---|---|---|---|---|
| 5-bromobenzimidazol-2-yl | 2 | 4 | 3 hrs | 25 | 265–268 |
| 1-methylbenzimidazol-2-yl | 2 | 4 | 48 hrs | 25 | 265–270 |
| 6-methoxyquinolin-8-yl | 2 | 4 | 30 min | 25 | 280 dec.$^b$ |

$^a$TEA = triethyl amine.
$^b$Purified by column chromatography using chloroform-methanol-acetic acid (18:5:1;V:V:V).

EXAMPLE 8

4-Guanidino-N-(1-N-methylcarbamylbenzimidazol-2-yl)benzamide (n=0; R$^1$=H; and HET=1-(N-methylcarbamyl)benzimidazol-2-yl)

The product of Example 1 (600 mg., 1.81 m. mol) of 520 mg. (9.07 m. mol) of methylisocyanate were added to 10 ml. of dry N-methyl-2-pyrrolidone and allowed to stir at room temperature for 24 hours. The mixture was poured into 200 ml. of diethyl ether and the resulting precipitate filtered and chromatographed on silica gel using chloroform-methanol-acetic acid (18:5:1;V:V:V) as the eluent. The fractions containing the product were combined, concentrated in vacuo to dryness and the residue triturated with methanol, 76 mg., m.p. 188°–190° C.

EXAMPLE 9

Using the procedure of Example 8 and starting with the product of Example 1 and the requisite alkylating agent and base, the following compounds were synthesized:

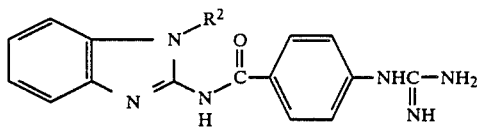

| R$^2$ | BASE | ALKYLATING AGENT | | REACTION TIME | REACTION TEMP. °C. | m.p., °C. |
|---|---|---|---|---|---|---|
| CH$_2$CONHCH(–C$_6$H$_4$–Cl) | KOC(CH$_3$)$_3$ (2)$^a$ | ClCH$_2$CONH(4-ClC$_6$H$_4$CH$_2$) | (5)$^b$ | 12 hrs | 100 | 197–200 |
| CH$_2$CON(C$_2$H$_5$)$_2$ | KOC(CH$_3$)$_3$ (1)$^a$ | ClCH$_2$CON(C$_2$H$_5$)$_2$ | (5)$^b$ | 2 hrs | 100 | 220–222 |
| CH$_2$CO$_2$C$_2$H$_5$ | KOC(CH$_3$)$_3$ (1)$^a$ | ClCH$_2$CO$_2$C$_2$H$_5$ | (5)$^b$ | 16 hrs | 100 | 210–212$^c$ |
| CH$_2$COC$_6$H$_5$ | K$_2$CO$_3$ (3)$^a$ | ClCH$_2$COC$_6$H$_5$ | (5)$^b$ | 12 hrs | 100 | 241–242$^c$ |
| (CH$_2$)$_2$C$_6$H$_5$ | K$_2$CO$_3$ (4)$^a$ | Br(CH$_2$)$_2$C$_6$H$_5$ | (6.5)$^b$ | 16 hrs | 100 | 285–290$^c$ |
| CH$_2$CONHC$_2$H$_5$ | KOC(CH$_3$)$_3$ (1)$^a$ | ClCH$_2$CONHC$_2$H$_5$ | (5)$^b$ | 16 hrs | 100 | 240–244$^c$ |

$^a$Equivalent of base to starting material.
$^b$Equivalent of alkylating agent to starting material.
$^c$Purified by chromatographing using chloroform-methanol-acetic acid (18:5:1;V:V:V).

We claim:

1. A compound of the formula

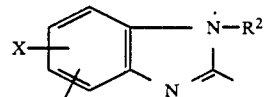

or a pharmaceutically acceptable salt thereof, wherein HET is benzimidazol-2-yl of the formula where X is hydrogen or methyl, Y is hydrogen, methyl, benzoyl, nitro, chloro, fluoro, bromo or methoxy and R$^2$ is hydrogen, (C$_1$–C$_3$)alkyl, phenethyl, phenacyl, N-(C$_1$–C$_3$)alkylcarbamylmethyl, N,N-di(C$_1$–C$_3$)alkylcarbamylmethyl, N-(C$_1$–C$_3$)alkylcarbamyl, (C$_1$–C$_3$)alkoxycarbonylmethyl or N-(p-chlorobenzyl)carbamylmethyl; n is an integer of 0 to 2; and R$^1$ is hydrogen or (C$_1$–C$_3$)alkyl.

2. A compound of claim 1, wherein R$^1$ is hydrogen and n is 0.

3. A compound of claim 2, wherein HET is a benzimidazol-2-yl of the formula
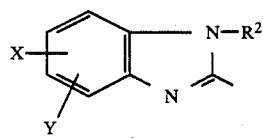
wherein, X is hydrogen.
4. The compound of claim 3, wherein Y and $R^2$ are each hydrogen.
5. The compound of claim 3, wherein Y is 5-nitro and $R^2$ is hydrogen.
6. The compound of claim 3, wherein Y is 5-chloro and $R^2$ is hydrogen.
7. The compound of claim 3, wherein Y is hydrogen and $R^2$ is N,N-diethylcarbamylmethyl.
* * * * *